United States Patent [19]
Harris et al.

[11] Patent Number: 5,356,806
[45] Date of Patent: Oct. 18, 1994

[54] IMMORTALIZED HUMAN CELL LINES CONTAINING EXOGENOUS CYTOCHROME P450

[75] Inventors: Curtis C. Harris, Bethesda; Harry V. Gelboin, Chevy Chase; Frank J. Gonzalez, Bethesda, all of Md.; Andrea M. A. Pfeifer, Vevey, Switzerland

[73] Assignees: The United States of America as represented by the Department of Health and Human Services, Washington, D.C.; Nestec, S.A.

[21] Appl. No.: 869,818

[22] Filed: Apr. 13, 1992

Related U.S. Application Data

[63] Continuation-in-part of Ser. No. 787,777, Nov. 6, 1991, Pat. No. 5,164,313, and a continuation-in-part of Ser. No. 636,712, Jan. 2, 1991, which is a continuation-in-part of Ser. No. 265,883, Nov. 1, 1988, abandoned, which is a continuation-in-part of Ser. No. 114,508, Oct. 30, 1987, Pat. No. 4,885,238, said Ser. No. 787,777, is a continuation-in-part of Ser. No. 58,387, Jun. 5, 1987, abandoned.

[51] Int. Cl.$^5$ .............................................. C12N 5/10
[52] U.S. Cl. .............................. 435/240.2; 435/69.1; 435/172.2
[58] Field of Search .................... 435/7.21, 69.1, 171.2, 435/172.3, 240.2, 59, 70

[56] References Cited

U.S. PATENT DOCUMENTS

| | | | |
|---|---|---|---|
| 4,816,395 | 3/1989 | Hancock | 435/29 |
| 4,885,238 | 12/1989 | Reddel | 435/29 |
| 5,164,313 | 11/1992 | Gelboin | 435/189 |

OTHER PUBLICATIONS

Arthur I. Grayzel, et al., "The Effects of Inhibitors of Protein Synthesis on the Synthesis of Heme in Rabbit Reticulocytes", *Biochemical and Biophysical Research Communications*, 28(5) (1967).

R. C. Garner and A. E. M. McLean, "Separation of HAEM Incorporation from Protein Synthesis in Liver Microsomes", *Biochemical and Biophysical Research Communications*, 37(6) :883–887 (1969).

K. W. Bock and P. Siekevitz, "Turnover of HEME and Protein Moieties of Rat Liver Microsomal Cytochrome $b_5$," *Biochemical and Biophysical Research Communications*, 41(2) :374–380 (1970).

Manford K. Patterson, Jr., "Measurement of Growth and Viability of Cells in Culture", *Methods in Enzymology*, 58:141–152 (1979).

Harry V. Gelboin, "Benzo[a]Pyrene Metabolism, Activation, and Carcinogenesis: Role and Regulation of Mixed–Function Oxidases and Related Enzymes," *Physiological Reviews*, 60(4) :1107–1166 (1980).

Gwen S. Duthu, et al., "Characterization of NADPH-Cytochrome P-450 Reductase in a Mouse Hepatoma Cell Line", *Biol. Abstr.*, 76(10):#73560 (1983).

John F. Lechner, et al., "Differential Control by Platelet Factors of Squamous Differentiation in Normal and Malignant Human Bronchial Epithelial Cells," *Cancer Research*, 43:5915–5921 (1983).

Shioko Kimura, et al., "The Murine Ah Locus," *The Journal of Biological Chemistry*, 259(17):10705–10713 (1984).

Sekhar Chakrabarti, et al., "Vaccinia Virus Expression Vector: Coexpression of β-Galactosidase Provides (List continued on next page.)

Primary Examiner—Richard A. Schwartz
Assistant Examiner—Gary L. Brown
Attorney, Agent, or Firm—Townsend and Townsend Khourie and Crew

[57] ABSTRACT

Non-tumorigenic, human bronchial epithelial cell lines are provided wherein the cell lines are capable of expressing cytochrome P450 genes which have been inserted into the cell lines. Also provided are methods and kits for identifying potential mutagens, cytotoxins, carcinogens, and chemotherapeutic agents utilizing these cell lines.

3 Claims, 9 Drawing Sheets

OTHER PUBLICATIONS

Visual Screening of Recombinant Virus Plaques", *Molecular and Cellular Biology*, 5(12):3403–3409 (1985).

Pietro Ghezzi, et al., "Role of Reactive Oxygen Intermediates in the Interferon-Mediated Depression of Hepatic Drug Metabolism and Protective Effect of N-Acetylcysteine in Mice", *Biological Abstracts*, 80(12):AB-961:#91194 (1985).

John F. Lechner and Moira A. LaVeck, "A Serum-Free Method for Culturing Normal Human Bronchial Epithelial Cells at Clonal Density", *Journal of Tissue Culture Methods*, 9(2):43–48 (1985).

Kenji Oeda, et al., "Expression of Rat Liver Cytochrome P–450MC cDNA in *Saccharomyces cerevisiae*," *DNA*, 4(3):203–210 (1985).

Hiroyuki Sadano and Tsuneo Omura, "Incorporation of Heme to Microcomal Cytochrome P–450 in the Absence of Protein Biosynthesis", *J. Biochem.*, 98(5):1321–1331 (1985).

William T. Wickner and Harvey F. Lodish, "Multiple Mechanisms of Protein Insertion Into and Across Membranes", *Science*, 230:400–406 (1985).

George H. Yoakum, et al., "Transformation of Human Bronchial Epithelial Cells Transfected by Harvey ras Oncogene", *Science*, 227:1174–1178 (1985).

Philippe H. Beaune, et al., "Isolation and Sequence Determination of a cDNA Clone Related to Human Cytochrome P–450 nifedipine oxidase", *Proc. Natl. Acad. Sci. USA*, 83:8064–8068 (1986).

Anil K. Jaiswal, et al., "Human $P_3 450$: cDNA and Complete Amino Acid Sequence", *Nucleic Acids Research*, 14(16):6773–6774 (1986).

Y. Ke. et al., "Human Bronchial Epithelial Cells Transformed by SV40 Gene(s) Retain the Ability to Undergo Terminal Squamous Differentiation," *J. Cell Biol.*, 103(2): 27a:#95 (1986).

M. Mackett and G. L. Smith, "Vaccinia Virus Expression Vectors", *J. Gen. Virol.*, 67:2067–2082 (1986).

Tohru Masui, et al., "Growth and Differentiation of Normal and Transformed Human Bronchial Epithelial Cells", *Journal of Cellular Physiology Supplement*, 4:73–81 (1986).

Toshitaro Nakagawa, et al., "Sodium N-Butyrate Modulates the Transcription and Posttranscriptional Processing of the Calcitonin Gene in Human Medullary Thyroid Carcinoma", *Federation Proceeding*, 46:718:#2352 (1987).

R. R. Reddel, et al., "Human Mesothelial Cells are Transformed by Transfection with SV40 Large T Antigen Gene", *J. Cell Biol.*, 103(2): 27a:#94 (1986).

Byung–Joon Song, et al., "Complementary DNA and Protein Sequences of Ethanol–Inducible Rat and Human Cytochrome P–450s", *The Journal of Biological Chemistry*, 261(35):16689–16697 (1986).

Edward B. Stephens, et al., "Surface Expression of Viral Glycoproteins is Polarized in Epithelial Cells Infected with Recombinant Vaccinia Viral Vectors", *Biol. Abstr.*, 81(12):AB-560:#112680 (1986).

Mauricio X. Zuber, et al., "Expression of Bovine 17α–Hydroxylase Cytochrome P–450 cDNA in Nonsteroidogenic (COS 1) Cells", *Science*, 234:1259–1261 (1986).

Narayana Battula, et al., "Expression of $P_1$–450 and $P_3$–450 DNA coding sequences as Enzymatically Active Cytochromes P–450 in Mammalian Cells", *Proc. Natl. Acad. Sci. USA*, 84:4073–4077 (1987).

Douglas E. Brash et al., "Strontium Phosphate Transfection of Human Cells in Primary Culture: Stable Expression of the Simian Virus 40 Large–T–Antigen Gene in Primary Human Bronchial Epithelial Cells", *Molecular and Cellualar Biology*, 7(5):2031–2034 (1987).

B. I. Gerwin, et al., "Growth Factor Production by Normal Human Mesothelial Cells and Mesothelioma Cell Lines", *European Association for Cancer*, p. 1752 (1987).

Brenda Gerwin, et al., "Response to Growth Factors by Normal Human Mesothelial Cell Lines and Their Autocrine Production by Human Mesothelioma Cell Lines",*J. Cell. Biochem.*, Supplement 11, Abstract A217, p. 58 (1987).

Shioko Kimura, et al., "cDNA and Amino Acid sequences of two members of the Human P450IIC Gene Subfamily", *Nucleic Acids Research*, 15(23):10053–10054 (1987).

J. F. Lechner, et al., "Normal Human Mesothelial Cells are Responsive to Unusual Combinations of Growth Factors", *Proceedings of AACR*, 28:60:#240 (1987).

R. Reddel, et al., "Development of Non–Tumorigenic Human Mesothelial Cell Lines with Transfected SV40 Large T Antigen Gene", *European Association for Cancer*, p. 1794 (1987).

R. R. Reddel, et al., "Establishment of Non–Tumorigenic Human Bronchial Epithelial Cell Lines", *Proc. Amer. Assoc. Cancer Res.*, 28:118:#469 (1987).

(List continued on next page.)

OTHER PUBLICATIONS

J. S. Rhim, et al., "An In Vitro Multi-Step Model for Human Epithelial Cell Carcinogenesis", *Proc. Amer. Assoc. Cancer Res.*, 28:120:#475 (1987).

Sasajima, et al., "Effects of Tumor Promoters and Co-carcinogens on Growth and Differentiation of Cultured Human Esophageal Epithelial Cells", *J. National Cancer Institute*, 78(3):419-423 (1987).

Diane R. Umbenhauer, et al., "Cloning and Sequence Determination of a Complementary DNA Related to Human Liver Microsomal Cytochrome P-450 S-Mephenytoin 4-Hydroxylase", *Biochemistry*, 26:1094-1099 (1987).

Paul Amstad, et al., "Neoplastic Transformation of a Human Bronchial Epithelial Cell Line by a Recombinant Retrovirus Encoding Viral Harvey ras", *Molecular Carcinogenis*, 1:151-160 (1988).

Johannes Doehmer, et al. "Stable Expression of Rat Cytochrome P-450IIB1 cDNA in Chinese Hamster Cells (V79) and Metabolic Activation of Aflatoxin $B_1$," *Proc. Natl. Acad. Sci. USA*, 85:5769-5773 (1988).

Frank J. Gonzales, et al., "Human Debrisoquine 4-Hydroxylase (P450IID1): cDNA and Deduced Amino Acid Sequence and Assignment of the CYP2D Locus to Chromosome 22", *Genomics*, 2:174-179 (1988).

Frank J. Gonzalez, et al., "Human P450PCN1: Sequence, Chromosome Localization, and Direct Evidence through cDNA Expression that P450PCN1 is Nifedipine Oxidase", *DNA*, 7(2):79-86 (1988).

Roger R. Reddel, et al., "Human Bronchial Epithelial Cells Neoplastically Transformed by v-Ki-ras: Altered Response to Inducers of Terminal Squamous Differentiation", *Oncogene Research*, 3:401-408 (1988).

Roger R. Reddel, et al., "Transformation of Human Brochial Epithelial Cells by Infection with SV40 or Adenovirus-12 SV40 Hybrid Virus, or Transfection via Stronitum Phosphate Coprecipitation with a Plasmid Containing SV40 Early Region Genes", *Cancer Research*, 48:1904-1909 (1988).

Morio Umeno, et al., "Human Ethanol-Inducible P450IIE1: Complete Gene Sequence, Promoter Characterization, Chromosome Mapping, and cDNA-Directed Expression", *Biochemistry*, 27:9006-9013 (1988).

R. Daniel Bonfil, et al., "Invasive and Metastatic Potential of a v-Ha-ras-Transformed Human Bronchial Epithelial Cell Line", *Journal of the National Cancer Institute*, 81(8):587-594 (1989).

C. L. Crespi, et al., "Transfection of a Human Cytochrome P-450 Gene into the Human Lymphoblastoid Cell Line, AHH-1, and use of the Recombinant Cell Line in Gene Mutation assays", *Carcinogenesis*, 10(2):295-301 (1989).

Robin L. Davies, et al., "Development of a Human Cell Line by Selection and Drug-Metabolizing Gene Transfection with Increased Capacity to Activate Promutatgens",*Carcinogenesis*, 10(5):885-891 (1989).

Andrea M. A. Pfeifer, et al., "Control of Growth and Squamous Differention in Normal Human Brochial Epithelial Cells by Chemical and Biological Modifiers and Transferred Genes", *Environmental Health Perspectives*, 80:209-220 (1989).

A. M. A. Pfeifer, et al., "Cooperation of c-raf-1 and c-myc Protooncogenes in the Neoplastic Transformation of Simian Virus 40 Large Tumor Antigen-Immortalized Human Bronchial Epithalial Cells", *Proc. Natl. Acad. Sci. USA*, 86:10075-10079 (1989).

Roger R. Reddel, et al., "Tumorigenicity of Human Mesothelial Cell Line Transfected with EJ-ras Oncogene,"*Journal of the National Cancer Institute*, 81(12):945-948 (1989).

Hitoshi Ura, et al., "Expression of Type IV Collagenase and Procollagen Genes and its Correlation with the Tumorigenic, Invasive, and Metastatic Abilities of Oncogene-Transformed Human Bronchial Epithelial Cells", *Cancer Research*, 49:4615-4621 (1989).

C. L. Crespi, et al., "The Development of a Panel of Human Cell Lines Expressing Specific Human Cytochrome P450 cDNAs",*Progress in Clinical and Biological Research*, 340B:97-106, Mendelsohn and Albertini (eds). Wiley-Liss: New York, (1990).

Charles L. Crespi, et al., "Human Cytochrome P450IIA3: cDNA Sequence, Role of the Enzyme in the Metabolic Activation of Promutagens, Comparison to Nitrosamine Activation by Human Cytochrome P450IIE1", *Carcinogenesis*, 11(8):1293-1300 (1990).

Brenda I. Gerwin, et al., "TGF-$\beta_1$ Modulation of Urokinase and PAI-1 expression in Human Bronchial Epithelial Cells", *Am. J. Physiol*, 259:L262-269 (1990).

Bernard Moss, "Poxviridae and their Replication", *Vi-*

(List continued on next page.)

OTHER PUBLICATIONS

*rology*, 2nd Ed., B. N. Fields (ed.), Raven Press, Ltd.: New York, pp. 2079–2111 (1990).

Shigeru Yamano, et al., "The CYP2A3 Gene Product Catalyzes Coumarin 7–Hydroxylation in Human Liver Microsomes", *Biochemistry*, 29:1322–1329 (1990).

Narayana Battula, et al., "Cytochroma P4501A2 Constitutively Expressed from Transduced DNA Mediates Metabolic Activation and DNA–Adduct Formation of Aromatic Amine Carcinogens in NIH 3T3 Cells", *Molecular Carcinogenesis*, 4:407–414 (1991).

Ronald W. Estabrook, et al., "The Heterologous Expression of the Cytochromes P450: A New Approach for the Study of Enzyme activities and Regulation", *Adv. Enzyme Regul.*, 31:365–383 (1991).

Monica Hollstein, et al., "p53 Mutations in Human Cancers", *Science*, 253:49–53 (1991).

Teresa A. Lehman, et al., "Oncogenes and Tumor–Suppressor Genes", *Environmental Health Perspectives*, 93:133–144 (1991).

A. M. A. Pfeifer, et al. "Human Bronchial Epithial Cells Transformed by the c–raf–1 and c–myc Protooncogenes Induce Multidifferentiated Carcinomas in Nude Mice: a Model for Lung Carcinogenesis", *Cancer Research*, 51:3793–3801 (1991).

ly active cytochromes P450 in mammalian cells. The invention also is related to immortalized human bronchial epithelial cells containing various cytochrome P450 genes and the uses of these cells.

IMMORTALIZED HUMAN CELL LINES CONTAINING EXOGENOUS CYTOCHROME P450

CROSS-REFERENCE TO RELATED APPLICATIONS

This application is a continuation-in-part application of Ser. No. 07/787,777, filed on Nov. 6, 1991, now U.S. Pat. No. 5,164,313, which was a continuation-in-part application of Ser. No. 07/058,387, filed on Jun. 5, 1987, now abandoned. This application also is a continuation-in-part application of Ser. No. 07/636,712, filed on Jan. 2, 1991, which was a continuation-in-part application of Ser. No. 07/265,883, filed on Nov. 1, 1988, which was a continuation-in-part application of Ser. No. 07/114,508, filed on Oct. 30, 1987, now issued as U.S. Pat. No. 4,885,238. These documents are incorporated herein by reference.

BACKGROUND OF THE INVENTION

The present invention is related to the construction and application of recombinant vectors containing DNA sequences for encoding, and efficient expression of, enzymatically active cytochromes P450 in mammalian cells. The invention also is related to immortalized human bronchial epithelial cells containing various cytochrome P450 genes and the uses of these cells.

The cytochromes P450 are a large family of hemoprotein enzymes capable of metabolizing xenobiotics such as drugs, carcinogens and environmental pollutants as well as endobiotics such as steriods, fatty acids and prostaglandins. Some members of the cytochrome P450 family are inducible in both animals and cultured cells, while other constitutive forms are non-inducible. This group of enzymes carry out beneficial metabolic activities by detoxification of xenobiotics as well as harmful metabolic conversion of xenobiotics to toxic, mutagenic and carcinogenic forms (Gelboin, *Physiol. Rev.*, 60:1107–1166, 1980).

In animals, multiple molecular forms of cytochrome P450s are expressed simultaneously and they all exhibit common physical and biological properties. The multiplicity and common properties of cytochromes P450 make it difficult to separate their different forms, especially the minor forms. Even in situations where P450 cytochromes have been isolated in purified form by conventional enzyme purification procedures, they have been removed from the natural biological membrane association and therefore require the addition of NADPH-cytochrome P450 reductase and other cell fractions for enzymatic activity. These additional factors have prevented a clearer understanding of the role and function of the individual cytochrome forms in metabolism, detoxification, and activation of both xenobiotic and endobiotic substrates.

Toxicological testing of drugs, potential carcinogens, food products, food additives and food contaminants has been performed in animals and more recently in in vitro systems, such as bacteria (Ames test) and animal cell culture models. These systems are disadvantaged since they do not have human-specific metabolism. Therefore, extrapolation to determine the human risk is difficult and potentially inaccurate. The bacterial test systems and some of the animal cell culture models lack complete metabolic activity and would not detect any harmful compounds which depend upon activation by metabolic pathways, for example, by the cytochrome P450 enzymes. In the past this situation was circumvented by adding metabolizing enzyme isolated from rat livers to the cultured animal cells. This approach poses two significant problems. First, the resulting metabolism is not necessarily the same as in man. Secondly, highly-reactive metabolites might not reach their target molecule and, consequently, escape detection.

Although human metabolizing enzymes have been introduced into a human cell line, this system suffers from serious deficiencies. (Crespi, *Progress in Clinical and Biological Research*, Vol. 340B Mendelsohn and Albertini (eds) Wiley-Liss, New York 97–106, 1990.) The human cells are lymphoblasts which do not constitute a major target tissue of cytotoxins, mutagens, or carcinogens and have no natural cytochrome P450 activity in the absence of inducers. In addition, other enzymes involved in the activation process, for example, epoxide hydrolase, are missing in these cells and must be introduced by gene transfer methodology. This system therefore comprises an artificial model with a questionable correlation to the in vivo situation.

SUMMARY OF THE INVENTION

Therefore, it is desirable to have an in vitro human cell line system which closely parallels the in vivo human condition. The present invention provides isolated non-tumorigenic human cell lines of bronchial epithelial cell origin with unlimited proliferative potential, resulting in immortalization.

In one embodiment of this invention a non-tumorigenic, human bronchial epithelial cell line or derivative thereof is provided wherein the cell line or derivative is capable of growing without senescence when cultured in vitro in growth medium and is capable of expressing an exogenous cytochrome P450 gene, homolog, or derivative thereof which has been inserted into the cell line. The gene can be inserted by transfection or infection. P450 genes expressed in this cell line include IA1, IA2, IIC9, IID6, IIE1, and/or IIIA4. A preferred cell line described by this invention is BEAS-2B-IA2, which is a BEAS-2B cell line transfected with the IA2 cytochrome P450 gene.

In another embodiment of this invention, various methods of utilizing the cell lines are described. For example, a method for identifying or testing the mutagenicity, cytotoxicity, or carcinogenicity of an agent is described which comprises the steps of: a) reacting, culturing, or contacting the cell line with an agent suspected of being a mutagen, cytotoxin, or carcinogen, and b) determining or monitoring those effects on, or changes in, the cell line which are indicative of mutagenicity, cytotoxicity, or carcinogenicity.

Also described by this invention is a method for identifying or testing the chemotherapeutic activity of an agent comprising the steps of: a) reacting, culturing, or contacting the cell line with an agent suspected of being a chemotherapeutic in the presence of a carcinogen, and b) determining or monitoring those effects on, or changes in, the cell line which are indicative of chemotherapeutic activity. The agent can be added prior to the carcinogen to measure the preventative effects of the agent.

In a further aspect of this invention, a method is provided for determining the metabolites activated by a carcinogen or xenobiotic comprising the steps of: a) reacting, culturing or contacting the cell line with the suspected carcinogen or xenobiotic, and b) identifying the metabolites and/or their effects.

Also provided is a diagnostic kit comprising the cell line for use in one of the methods.

In a further aspect of the invention, infectious recombinant vectors are provided which contain full-length cDNA sequences for cytochromes, such as P1-450 and P3-450 also known as CYP1A1 and CYP1A2, respectively. The present invention also provides systems which express enzymatically active cytochrome P450 proteins in human cells.

Various other objects and advantages of the present invention will become apparent from the Detailed Description of the Invention.

BRIEF DESCRIPTION OF THE DRAWINGS

These and other objects, features and many of the attendant advantages of the invention will be better understood upon a reading of the following detailed description when considered in connection with the accompanying drawings wherein.

DESCRIPTION OF THE INVENTION

Figure 1:
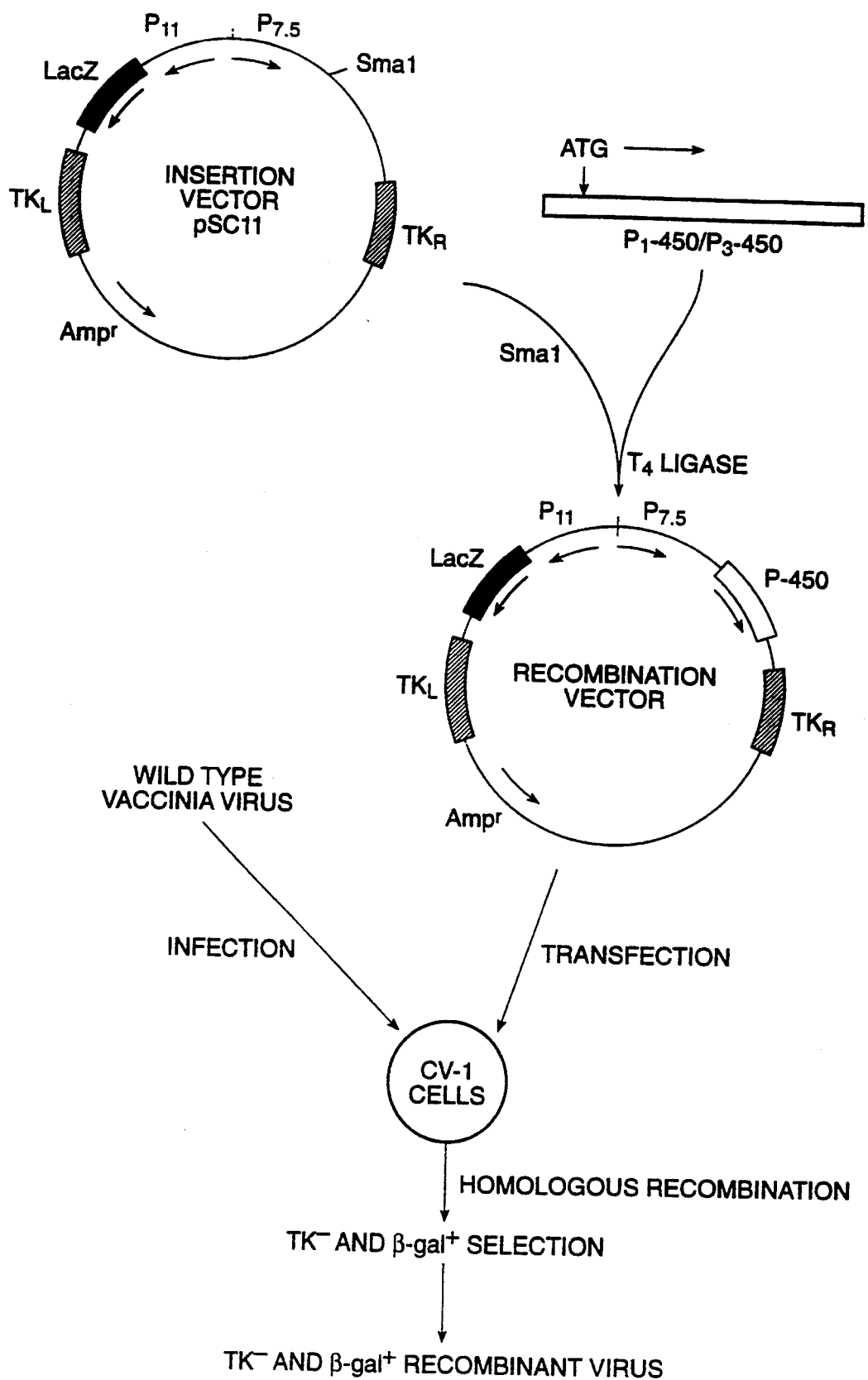
FIG. 1 shows the schematic construction of recombinant vaccinia viruses for expressing mouse cytochromes P1-450 and P3-450. P11 and 7.5, vaccinia transcriptional regulatory sequences for 11K and 7.5K polypeptides respectively; Lac Z, Escherichia Coli β-galactosidase gene; $TK_L$, and $TK_R$, split segments of vaccinia virus DNA from left and right positions of TK gene respectively. $Amp^r$ is ampicillin resistance gene.

The above and various other objects and advantages of the present invention are achieved by (a) constructing recombinant vectors containing cDNA sequences for encoding cytochrome P450 polypeptides so that mammalian, especially human, cells when infected with said recombinant vectors efficiently express the P450 polypeptides; and (b) providing functionally intact cell lines containing cytochrome polypeptides without requiring the extraneous addition of NADPH cytochrome P450 reductase for enzymatic activity.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

Bronchial Cell Lines

The immortalized human bronchial epithelial cell lines utilized in this invention are described in U.S. Pat. No. 4,885,238. These cell lines are prepared as follows.

Normal human bronchial epithelial (NHBE) cells were cultured from explants of necropsy tracheobronchial specimens from noncancerous individuals as described by Lechner, et al., *J. Tissue Culture Methods*, 9:43-48, 1985. The NHBE cells were infected with adenovirus-12 SV40 hybrid virus. In all cases the lifespan of these cultures was extended compared to NHBE; most of the cultures underwent a prolonged period of senescence referred to as "crisis". With continued culture, in some cases colonies of cells which had escaped senescence arose; such surviving colonies were subsequently passaged for extended periods of time and showed unlimited growth potential.

Like NHBE cells, but unlike bronchial carcinoma cells, some of the cell lines thus derived retained the capacity to undergo squamous differentiation in response to serum exposure. Injection of these cells into irradiated athymic nude mice did not result in formation of tumors after periods of up to nine months. Furthermore, these cell lines were found to be suitable recipients for transfection of additional genes and useful for testing the cytotoxicity potential of chemical and physical agents, the growth inhibition or promoting capability of biological agents, and squamous differentiating potential of chemical and biological agents.

Development of the BEAS-2B Cell Line

A preferred cell line for use in this invention is BEAS-2B which was prepared as follows. NHBE cells were cultured from explants of autopsy specimens from noncancerous individuals as described by Lechner, et al., *J. Tissue Culture Methods*, 9:43-48, 1985. The cells were cultured in a serum-free medium, LHC-9, harvested by trypsinization and seeded in 10 ml growth medium into 100 mm culture dishes (Lux, Miles Scientific, Naperville, Ill.) whose growth surfaces had been coated with a solution of bovine serum albumin, fibronectin and collagen (Lechner, et al., supra.).

Adenovirus 12-SV40 (Ad12SV40) hybrid virus (Schell, et al. *Proc. Natl. Acad. Sci. U.S.A.* 55:81–88, 1966) was grown in Vero cells as described by Rhim, et al., *Proc. Natl. Sci, U.S.A.*, 78:313–317, 1981. NHBE cells were exposed to the virus at 37° C. for four hours at a multiplicity of infection of approximately 100. When the cultures reached confluence, each dish was subcultured into two 75 cm² flasks. The cells were allowed to reach confluence again and then were re-fed twice weekly until transformed colonies appeared and the normal cells senesced. Senescence of the normal cells was accelerated by exposing the cultures to 1%

FCS in LHC-9 for 28 days (Lechner, et al., *Differentiation*, 25:229–237, 1984); all subsequent culture of these cells was in serum-free LHC-9 medium. Individual colonies were subcultured 41 days after the viral infection and cell strains thus derived from this experiment were designated BEAS-2.

Since BEAS-2B cells are derived from human bronchial epithelial cells which are most likely the progenitor cells of all types of lung cancer, BEAS-2B cells should represent the in vivo situation. They are capable of expressing IA1 and other enzymes involved in the activation process of carcinogens and mutagens, such as glutathione S-transferase, epoxide hydrolase, and NADPH cytochrome P450 reductase.

Cytochrome P450 Genes and Vectors

Genomic or cDNA clones encoding cytochrome P450 genes may be isolated from clone libraries using hybridization probes designed on the basis of the nucleotide or amino acid sequences for the desired gene. The probes can be constructed by chemical synthesis or by polymerase chain reactions using primers based upon sequence data to amplify DNA fragments from pools or libraries. (U.S. Pat. Nos. 4,683,195 and 4,683,202.) Nucleotide substitutions, deletions, additions, and the like also may be incorporated into the polynucleotides, so long as the ability of the polynucleotide to hybridize is not substantially disrupted. (Maniatis, et al, *Molecular Cloning: A Laboratory Manual*, 2nd Ed. 1989 and Berger and Kimmel, *Methods in Enzymology*, Volume 152, *Guide to Molecular Cloning Techniques* (1987). The clones may be expressed or the P450 gene of interest can be excised or synthesized for use in other systems. The sequences of various cDNA isolates are described for cytochrome P450IIC9 (Umbenhauer, et al., *Biochem.*, 26:1094–1099, 1987 and Kimura, et al., *Nucl. Acids Res.*, 15:10053–10054, 1987); P450IIE1 (Song, et al., *J. Biol. Chem.*, 261:16689–16697, 1986 and Umeno, et al, *Biochem.*, 27:9006–9013, 1988); and P450IIIA4 (Beaune, et al., *Proc. Natl. Acad. Sci. U.S.A.*, 83:8064–8068, 1986 and Gonzales, et al., *DNA*, 7:79–86 1988). Cytochrome P450IA2 is described by Jaiswal, et al., *Nucl. Acids Res.*, 14:6773–6774, 1986; IIA3 by Yamano, et al., *Biochem.*, 29:1322–1329, 1990; and IID6 by Gonzalez, et al., *Genomics*, 2:174–179, 1988.

The cytochrome P450 genes can be transferred into the cell lines by transfection of plasmid DNA or by retroviral infection. Transfection of cells can occur through those methods commonly used, such as calcium or strontium phosphate treatment microinjection, electroporation, or lipofection. For example, the cells may be injected with a molony-LTR driven promoter or lipofected with an adenovirus, vaccinia virus, HIV, or CMV-promoter construct. The transfected DNA plasmid can contain a selectable marker gene or be co-transfected with a plasmid containing a selectable marker, and in some cases, the retroviral vector contains a selectable marker gene. Where one or more selectable marker is transferred into the cells along with the P450 gene, the cell populations containing the P450 gene can be identified and enriched by selecting for the marker or markers. Markers typically are antibiotic resistant to such antibiotics as tetracycline, hygromycin, neomycin, and the like. Other markers can include thymidine kinase and the like.

Figure 7:
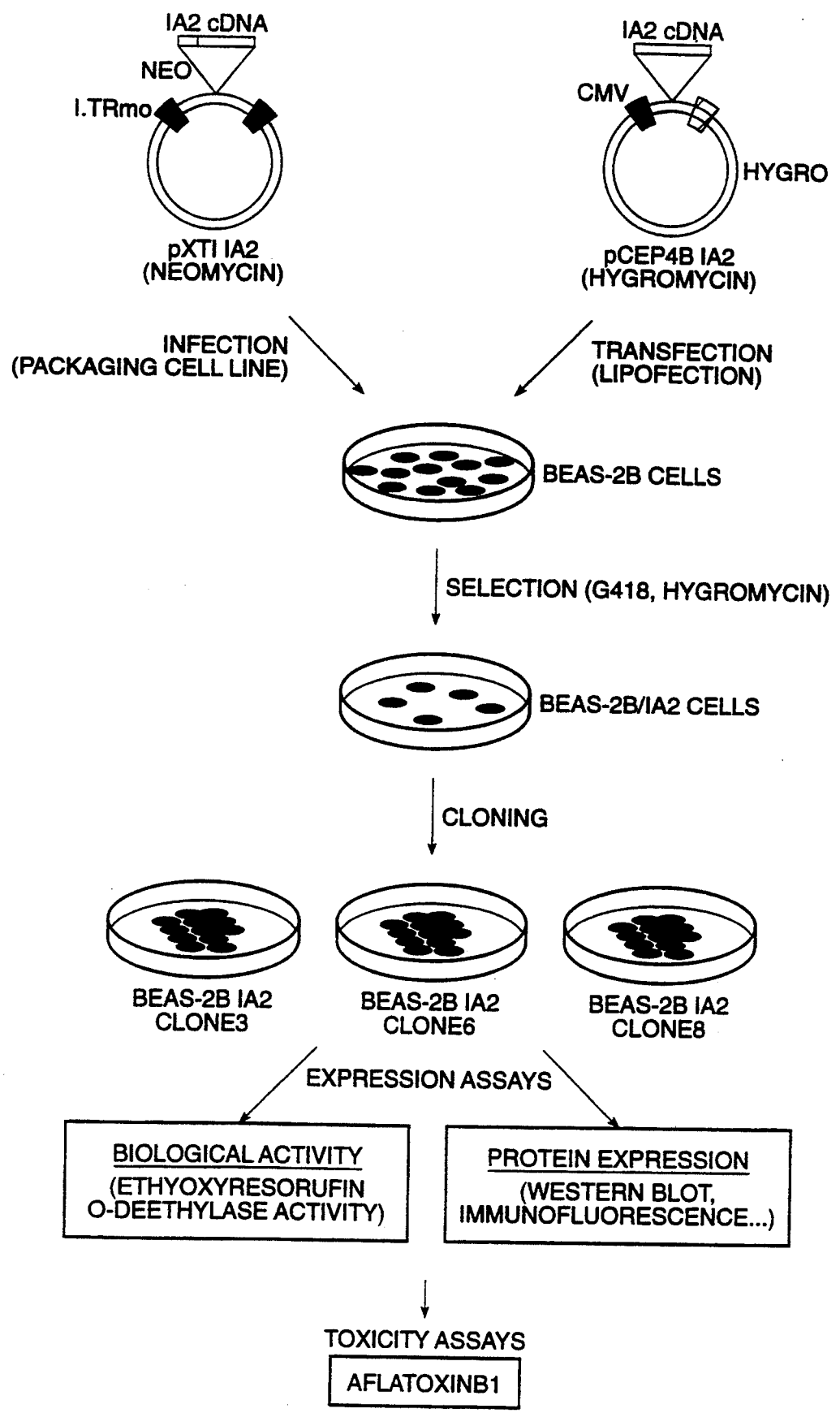
FIG. 7 shows the schematic construction of the recombinant vectors for expressing cytochrome P450 genes and the transfection of the vectors into the BEAS-2B cells.

Immortalized Human Bronchial Epithelial Cell Line Containing Cytochrome P450 Genes Complementary cDNAs for the cytochrome P450 enzymes, IA2, IIA3, IID6, IIE1, and IIIA4, were introduced by recombinant high titer amphotropic retroviruses into the BEAS-2B cells. These retroviruses were generated by cloning the corresponding cDNAs into a plasmid pXT1 (Boulter, et al., *Nucleic Acid*, 15:7194, 1987) and transfecting the recombinant plasmids into co-cultured packaging lines with amphotropic (PA317) and ecotropic envelopes (Psi2) using calcium phosphate precipitation (Bestwick, et al., *Proc. Natl. Acad. Sci. U.S.A.*, 85:5404–5408, 1988) (See FIG. 7).

After 10 days, virus was collected from confluent PA317/Psi2 cultures in serum free PC-1 medium (Ventrex Laboratories, Inc., Portland, Oreg.). The titers were determined on NIH3T3 cells and were expressed as neomycin resistant colonies/ml supernatant. The BEAS-2B cells were infected for 2 hours with the P450 viruses or the control virus, pXT1, in PC-1 medium supplemented with 8 $\mu$g/ml polybrene (Table 1).

TABLE 1

| Generation of high liter amphotropic P450 retroviruses ||| 
|---|---|---|
| Retrovirus | Titer | Metabolic Activity |
| IA2 | $10^5$ | AA, HAA, MeiQ, NNK, $AFB_1$, caffeine |
| IIA3 | $2 \times 10^5$ | DEN, DMN, NNK, $AFB_1$, coumarin |
| IID6 | $5 \times 10^4$ | buforol, debrisoquine, NNK |
| IIE1 | $10^5$ | DEN, DMN, NNK, Ethanol |
| IIIA4 | $6 \times 10^4$ | $AFB_1$, B(a)P 7,8-diol, nifedipine |

AA, aromatic amines; HAA, heterocyclic aromatic amines; NNK, 4-(methylnitrosamino)-1-(3-pyridyl)-1-butanone; $AFB_1$, aflatoxin $B_1$; DEN, diethylnitrosamine; DMN, dimethylnitrosamine; MeiQ, 2-amino-3,8-dimethyl-imidazo[4,5-f]quinoxaline.

An equal ratio of cells to colony forming units of the virus was employed. Forty-eight hours after infection the BEAS-2B cells were selected for G418 neomycin resistance with 125 $\mu$g/ml neomycin for 8 days. Subsequently, the cells were selected for the presence of the introduced genes by Western blot analysis. Exemplified for the P450IA2, the population and 3 clones (clone 8>clone 3>clone 6) expressed the protein corresponding to the respective P450 retrovirus. In accordance, clone 8 (cl 8) showed the highest sensitivity being up to 150 times more responsive to the cytotoxic effect and up to 250 times to the genotoxic effect of a model compound, $AFB_1$, than the control.

Figure 8:
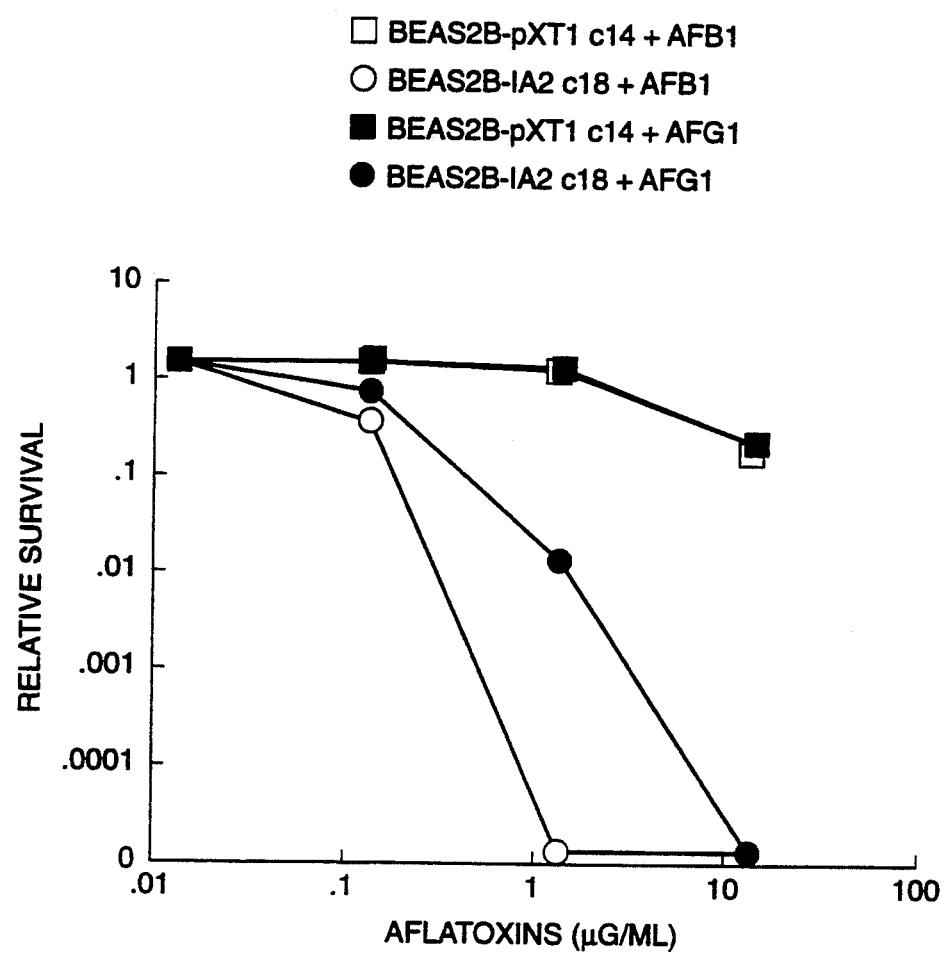
FIG. 8 shows the cytotoxicity of Aflatoxin $B_1$ or Aflatoxin $G_1$ in the BEAS-2B-pXT1 and BEAS-2B-IA2 lines.

FIG. 8 also shows the analysis of cytotoxicity for Aflatoxin $B_1$ or Aflatoxin $G_1$ on the BEAS-2B-pXT1 and BEAS-2B-IA2 clones. The cells were exposed to various concentrations of the mutagens for 28 hours. Each culture contained 250 cells per 60 mm dish. After 7–10 days, cytotoxicity was determined by measuring the colony number of each plate. The colony number of the mutagen-treated cultures was divided by the colony number of the untreated cultures to yield relative survival. Each time point reflects at least 3 independent experiments.

Table 2 gives the DNA-adduct formation with $AFB_1$. The formation was elevated by a factor of 1000 in clone 8.

TABLE 2

| Binding of [$^3$H]$AFB_1$ to cellular DNA ||| 
|---|---|---|
| Carcinogen exposure ($\mu$g/ml) | Adduct formation (pmol/mg DNA) ||
|  | BEAS-2B-pXT1 cl 4 | BEAS-2B-IA2 cl 8 |
| — | und. | und. |

TABLE 2-continued

| Carcinogen exposure (μg/ml) | Binding of [³H]AFB₁ to cellular DNA | |
|---|---|---|
| | Adduct formation (pmol/mg DNA) | |
| | BEAS-2B-pXT1 cl 4 | BEAS-2B-IA2 cl 8 |
| 0.1 | und. | 0.39 |
| 1.0 | 0.04 | 9.00 |

Approximatively $1 \cdot 10^7$ cells were exposed to 0.1 or 1.0 μg/ml [³H]AFB₁ (0.2 Ci/mmol) under the conditions of the cytotoxicity assay. Cellular DNA was isolated and binding was measured by liquid scintillation counting (und.: undetectable).

Utility of Cell Lines (1) Identification of potential chemotherapeutic drugs: These cells are useful for screening chemicals suitable for the treatment of cancer and related diseases, by growing them in vitro in medium containing the chemical to be tested and then, after a suitable period of exposure, determining whether and to what extent cytotoxicity has occurred, e.g., by trypan blue exclusion assay or related assays (Paterson, *Methods Enzymol.*, 58:141, 1979), or by growth assays such as colony formatting efficiency (MacDonald, et al., *Exp. Cell. Res.*, 50:417, 1968), all of which are standard techniques well known in the art. Once a potential chemotherapeutic is identified, it and the cells can be used in further studies, such as drug design. These cells also are useful in the identification of potential carcinogens.

(2) Studies of the control of squamous differentiation, and identification of chemical and biological agents which induce squamous differentiation: This is accomplished by assays previously described for normal human bronchial epithelial cells (Masui, *Proc. Natl. Sci. U.S.A.*, 83:2438, 1986). Some cells retain the ability to undergo squamous differentiation in response to serum. Induction of terminal differentiation may be an effective way of controlling the growth of cancer. Chemical and biological substances are screened for their ability to induce differentiation by adding them to the growth medium of these cells and then after a suitable time interval determining whether a complex of changes including cessation of DNA synthesis and the appearance of squamous morphology has occurred. The cells are also useful for studies for the biological mechanisms of squamous differentiation, and the existence of both serum-resistant and serum-sensitive cell lines enables comparisons and identification of genes involved in the process of differentiation.

(3) Studies of metabolism of carcinogens and other xenobiotics: Carcinogens and other xenobiotics may be added to the growth medium of these cells and then the appearance of metabolic products of these compounds may be monitored by techniques such as thin layer chromatography or high performance liquid chromatography and the like. The interaction of the compounds and/or their metabolites with DNA then is determined.

(4) Studies of DNA mutagenesis: Substances known or suspected to mutagens may be added to the growth medium of the cells and then mutations may be assayed, e.g., by detection of the appearance of drug resistant mutant cell colonies (Thompson, *Methods Enzymol.*, 58:308, 1979). Similarly, cell-mediated DNA mutagenesis, by co-cultivating the cells with cell types known or suspected to be capable of secreting mutagenic compounds (Hsu, et al., *Proc. Natl. Acad. Sci. U.S.A.*, 75:2003, 1978).

The P450 enzyme can also be linked to a mutagen detection assay such as the Ames Salmonella/microsome system for detecting or testing the mutagenic frequency induced by environmental pollutants, carcinogens and the like (Ames, et al., *Mut. Res.*, 31:347, 1975). Other standard methods well known in the art such as chromosome aberration and sister chromatid exchange induction in Chinese hamster ovary cells (Galloway, et al., *Environ. Mutagen.*, 7:1, 1985) or mouse lymphoma cell mutagenesis assays (Myhr, et al., *Prog. in Mut. Res.*, 5:555-568, 1985) can, of course, also be used for testing mutagenicity.

(5) Studies of chromosome damaging agents: Substances known or suspected to cause chromosomal damage may be added to the culture medium of these cell lines, and then the extent of chromosomal damage may be measured by techniques such as measurement of the frequency of sister chromatid exchange (Latt, et al., In: Tice, R. R. and Hollaender, A. *Sister Chromatid Exchanges*, New York: Plenum Press, pp. 11 ff., 1984).

(6) Studies of malignant transformation by chemical, physical and viral agents, and transferred genes including oncogenes, mutant tumor suppressor genes, and high molecular weight genomic DNA from tumors, using standard assays such as anchorage independent growth or tumor formation in athymic nude mice.

(7) Use of cells altered by transfer of oncogenes as in paragraph 6 above to screen for potential chemotherapeutic agents (by the techniques described in paragraph 1 above) especially those which may be specific for cells transformed by the activation of particular oncogenes, combination of oncogenes, or mutant tumor suppressor genes.

(8) Studies of cellular biochemistry, including changes in intracellular pH and calcium levels, as correlated with cell growth and action of exogenous agents including, but not limited to, those described in paragraphs 1 through 7 above. To study intracellular pH and calcium levels, cells in suitable culture vessels are exposed to fluorescent indicator dyes and then fluorescence emissions are detected with a fluorescence spectrophotometer (Grynkiewicz, et al., *J. Biol. Chem.*, 260:3440-3450, 1985).

(9) Studies of cellular responses to growth factors and production of growth factors: Identification and purification of growth factors important for growth and differentiation of human bronchial epithelial cells. These cells are particularly useful for such an application since they grow in serum-free media. Therefore, responses to growth factors can be studied in precisely defined growth media and any factors produced by the cells may be identified and purified without the complication of the presence of serum.

(10) Use of recombinant DNA expression vectors to produce proteins of interest. For example, the gene encoding a protein of therapeutic value may be recombined with controlling DNA segments (i.e. containing a promoter with or without an enhancer sequence), transferred into the cell (e.g., by strontium phosphate transfection) and then the protein produced may be harvested from the culture supernatant or a cellular extract by routine procedures well known in the art.

(11) Studies of intracellular communication, e.g., by dye scrape loading assays. To determine whether the cells growing in vitro have the ability to communicate via gap junctions; the cultures may be scraped, e.g. with a scalpel in the presence of a fluorescent dye in the growth medium. Cells at the edge of the wound are mechanically disrupted and therefore take up dye; whether intercellular communication has occurred may be ascertained by determining whether cells distant from the wound also contain dye.

(12) Characterization of cell surface antigens: The cells are incubated with an antibody against the cell surface antigen of interest, and then reacted with a second antibody which is conjugated to a fluorescent dye. The cells are then evaluated using a fluorescence activated cell sorter to determine whether they are fluorescent and therefore possess the cell surface antigen.

(13) Hybrid studies for identification of tumor suppressor activity (Stanbridge, et al., Science, 215:252–259, 1982). To determine whether these cell lines contain tumor suppressor genes, they are fused to malignant tumor cells. The presence of tumor suppressor genes is indicated by loss of malignancy, e.g., as detected by loss of ability to form tumors in athymic nude mice, in the hybrid cells.

(14) Identification of novel genes, including transforming genes in naturally occurring cancers described in paragraph 6 above, growth factor genes as described in paragraph 9 above, tumor suppressor genes as described in paragraph 13 above, using standard molecular biological techniques (Davis, et al., Methods in Molecular Biology, New York: Elseveier, 1986) and techniques such as cDNA subtraction cloning and the like. These genes or their derivatives can be used in gene therapy.

Of course, a kit for screening carcinogenic or antineoplastic agents and for any other usage as described herein, is easily assembled, comprising container(s) containing the cell line(s) of the present invention. Other components routinely found in such kits may also be included with instructions for performing the test.

Preparation and expression of P1-450 and P3-450 in vaccinia viruses is described below.

Enzymes and Chemicals

Restriction endonuclease, DNA polymerase 1 and its Klenow fragment, and T4 DNA ligase were purchased from commercial sources and used according to the manufacturers' specifications. 5-Bromo-4-Chloro-3-Indolyl-$\beta$-D-galactosidase (X-gal) was purchased from Boehringer Mannheim (Smith et al, Biotechniques, November/December:306–312, 1984). C-acetanilide (31.7 mCi/mmole) was bought from California Bionuclear.

Viruses and Cells

Vaccinia virus (strain WR) HeLa cells, CV-1 cells, BSC-1 cells, and human TK$^-$ 143 cells were obtained from NIH, Bethesda, Md. The virus was grown in HeLa cells and purified from cytoplasmic extracts by sucrose density gradient centrifugation following the procedures described by Joklik, Virology, 18:9–18, 1962. All cells were grown in Dulbecco modified Eagle's minimal essential medium containing 10% fetal bovine serum and TK$^-$ cells in addition had 25 $\mu$g of BrdUrd per ml.

Vectors and DNA

Coexpression insertion vector pSC-11 (Chakrabarti, et al, Mol. Cell. Biol., 5:3403–3409, 1985), and complementary DNA clones of cytochrome P1-450 and P3-450 (Kimura, et al., J. Biol. Chem., 259:10705–10713, 1984) were employed in the construction of the recombinants. The plasmids were grown in bacteria and their DNAs purified by two sequential centrifugations on CsCl-EtBr equilibrium density gradients. DNA fragments were separated on agarose gels and purified by electroelution. Other recombinant DNA procedures were carried out by standard procedures (Maniatis et al, Molecular Cloning: A Laboratory Manual, Cold Spring Harbor: New York, 1982). Vaccinia virus DNA was extracted from the purified virions as described by Garon, et al., Proc. Natl. Acad. Sci., U.S.A., 75:4865–4867, 1978.

Infection, Transfection and Isolation of Recombinant Viruses

The procedures were carried out essentially as described by B. Moss and colleagues (Mackett, et al., J. Virol., 49:857–864, 1984; Smith, supra.; Mackett, et al., Proc. Natl. Acad. Sci. U.S.A., 79:7415–7419, 1982). Subconfluent CV-1 monkey kidney cells infected with wild type vaccinia virus (WT-VV) were transfected with 10 $\mu$g of recombination vector and 1 $\mu$g of wild type vaccinia virus DNA. Two days after incubation, the recombinant TK$^-$ viruses formed within the cells were distinguished from the wild type by a plaque assay on TK$^-$ cells in the presence of BrdUrd (Chakrabarti, et al., 1985, supra.). The TK$^-$ cells with the TK$^-$ plaques were overlaid with agar containing 400 $\mu$g X-gal per ml to check for concomitant expression of $\beta$-galactosidase and also to distinguish TK$^-$ recombinants from TK$^-$ mutants. The TK$^-$, $\beta$-gal+recombinants were purified by two cycles of selection. The recombinants were then screened for the presence of P1-450 and P3-450 cDNA inserts by dot blot hybridization (Macket, et al., 1982, supra.) and the virus stocks prepared in HeLa cells.

Protein Analysis by Immunoblotting

Cells were harvested by scraping and the lysates were prepared by three freeze-thaw cycles and brief sonication in a buffer containing 0.02M Tris-HCl, pH 7.5,+0.25M sucrose. Protein concentration was determined by Lowry's method (Lowry, et al., J. Bio. Chem., 193:265–275, 1951). Electrophoresis in 7.5% polyacrylamide gels in the presence of NaDodSO$_4$ was performed as described by Laemmli (Nature, 227:680–685, 1970). Prestained protein molecular weight standards (Bethesda Research Laboratories) were used to estimate the size of the polypeptides. The electrophoresed proteins were transferred to nitrocellulose membranes and the transferred proteins detected by Western blotting (Towbin, et al., Proc. Natl. Acad. Sci. U.S.A., 76:4350–4354, 1979) using a mixture of rabbit antisera against P-450c and P-450d. The P-450c and the P-450d forms are the rat homologues of mouse P1-450 and P3-450, respectively. These proteins share a high degree of homology and their antisera cross-react with each other. The immunoblots were detected by incubating with goat anti-rabbit immunoglobulin G conjugated with alkaline phosphatase (KPL Labs, Gaithersburg, Md.) in conjunction with the chromogenic substrate 5-bromo-4-chloro-3-indolyl-phosphate/p-nitro blue tetrazolium chloride.

Measurement of Co-Reduced Difference Spectra

Microsomal fractions were prepared from the cell lysates. The lysates were centrifuged at about 700 g for 10 minutes and the supernatant was recentrifuged at about 8,000 g for 10 minutes. The resulting 8,000 g supernatant was centrifuged again at about 100,000 g for 60 minutes to pellet the microsomes. The microsomal fraction was suspended in 0.11M potassium phosphate buffer, pH 7.5, containing 20% glycerol. For difference spectra, the microsomal fraction was solubilized with 0.14% emulgen 913 (15 minutes), centrifuged at 100,000 g for 60 minutes and the supernatant used. The spectra were measured in an Aminco Instruments Company model DW-2a spectrophotometer as described by Omura, et al., *J. Biol. Chem.*, 239:2370–2378, 1964.

Enzyme Assays

Aryl hydrocarbon hydroxylase (AHH) activity was determined by measurement of the fluorescence of phenolic metabolites formed from benzo(a)pyrene, Nebert, et al., *J. Biol. Chem.*, 243:6242–6249, 1968. The reaction mixture contained in 1.0 ml: 50 µmol Tris-HCl, pH 7.5, 0.3 µmol $MgCl_2$; 0.6 µmol NADPH; 100 nmol benzo(a)pyrene and 400 µg of cell homogenate. AHH activity is expressed as pmols of product equivalent to 3-OH benzo(a)pyrene formed per mg protein per minute. Acetanilide hydroxylase activity was determined by measuring the conversion of $^{14}$-C acetanilide to its hydroxylated derivatives. The substrate and its metabolites were separated by silica gel thin layer chromatography (TLC) following standard procedures. The assay was carried out in a final volume of 1.0 ml containing: 50 µmol Tris-HCl, pH 7.5, 0.3 µmol $MgCl_2$, 0.6 µmol NADPH, 2 µmol $^{14}$C-acetanilide at a specific activity of 1.0 m Ci/m mole and 500 µg of total cell homogenate. The enzyme activity is expressed as picomoles of product formed per mg of protein/minute. An aliquot of the reaction product in methanol was spotted on 250 µ thin-layer silica gel plate (Whatman) and eluted with 95% chloroform+5% methanol. The Rf values for acetanilide and 4-hydroxy acetanilide under these conditions is about 0.74 and 0.2, respectively. The gel plate was autoradiographed and product quantified by counting the radioactivity after scraping from plate.

Construction of Plasmids and Virus Recombinants

Construction of the chimeric genes containing the transcriptional regulatory signals and RNA start site of vaccinia virus genes, the translation start site of the coding sequences of the mouse P1-450 and P3-450, and the incorporation of these sequences into the wild type vaccinia virus to form recombinants, are diagrammatically presented in FIG. 1. The starting plasmid in the construction sequence of generating the recombinant virus is the insertion vector pSC-11. This coexpression insertion vector contains: the Escherichia coli β-galactosidase gene under the control of vaccinia promoter for 11K protein, a second promoter for 7.5K protein for transcription of coding sequences, a unique Sma 1 site down stream of the 7.5K promoter for the insertion of foreign protein coding sequences, and flanking vaccinia virus TK sequences for homologous recombination inside infected cells (Mackett, et al., 1984, supra.). A 2.6 Kb full-length cDNA for cytochrome P1-450 and 1.9 Kb full-length cDNA for cytochrome P3-450 (Kimura, et al., 1984, supra.) were modified and inserted into the unique Sma 1 site of the insertion plasmid to form the recombination vectors containing the individual P1-450 and P3-450. Selection of the recombination plasmids containing the P1-450 and P3-450 inserts in correct orientation was accomplished by restriction enzyme mapping. The two recombination plasmids were then individually used to transfect CV-1 cells previously infected with WT-VV. Homologous recombination between vaccinia TK sequences in the recombination plasmid and the virus genome resultant in insertion of the P450 and the β-galactosidase sequences into the vaccinia virus. The progeny viruses were then plaque assayed on TK$^-$ cells in the presence of BrdUrd to select for TK$^-$ virus and overlaid with agar containing X-gal (chromogenic substrate for β-galactosidase) to select for β-gal$^+$ virus. The presence of the P1-450 and P3-450 inserts in the TK$^-$ and β-gal$^+$ recombinants was confirmed by dot blot hybridization (Mackettt, et al., *Proc. Natl. Acad. Sci., U.S.A.*, 79:7415–7419, 1982). After two sequential plaque purifications the recombinant virus stocks were designated VV-P1 and VV-P3, respectively.

A deposit of the recombinant vaccinia virus containing the entire coding sequence for the P1-450 and P3-450 has been made at the American Type Culture Collection (ATTC), Rockville, Md., under the accession numbers VR-2168 and VR2169, respectively. The BEAS-2B cell line also was deposited at the American Type Culture Collection (ATCC), Rockville, Md. on Dec. 16, 1987, as CRL 9609. The deposits shall be viably maintained, replacing if they become non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

Analysis of P1-450 and P3-450 Proteins in VV-P1 and VV-P3 Infected Cells

Figure 2A:
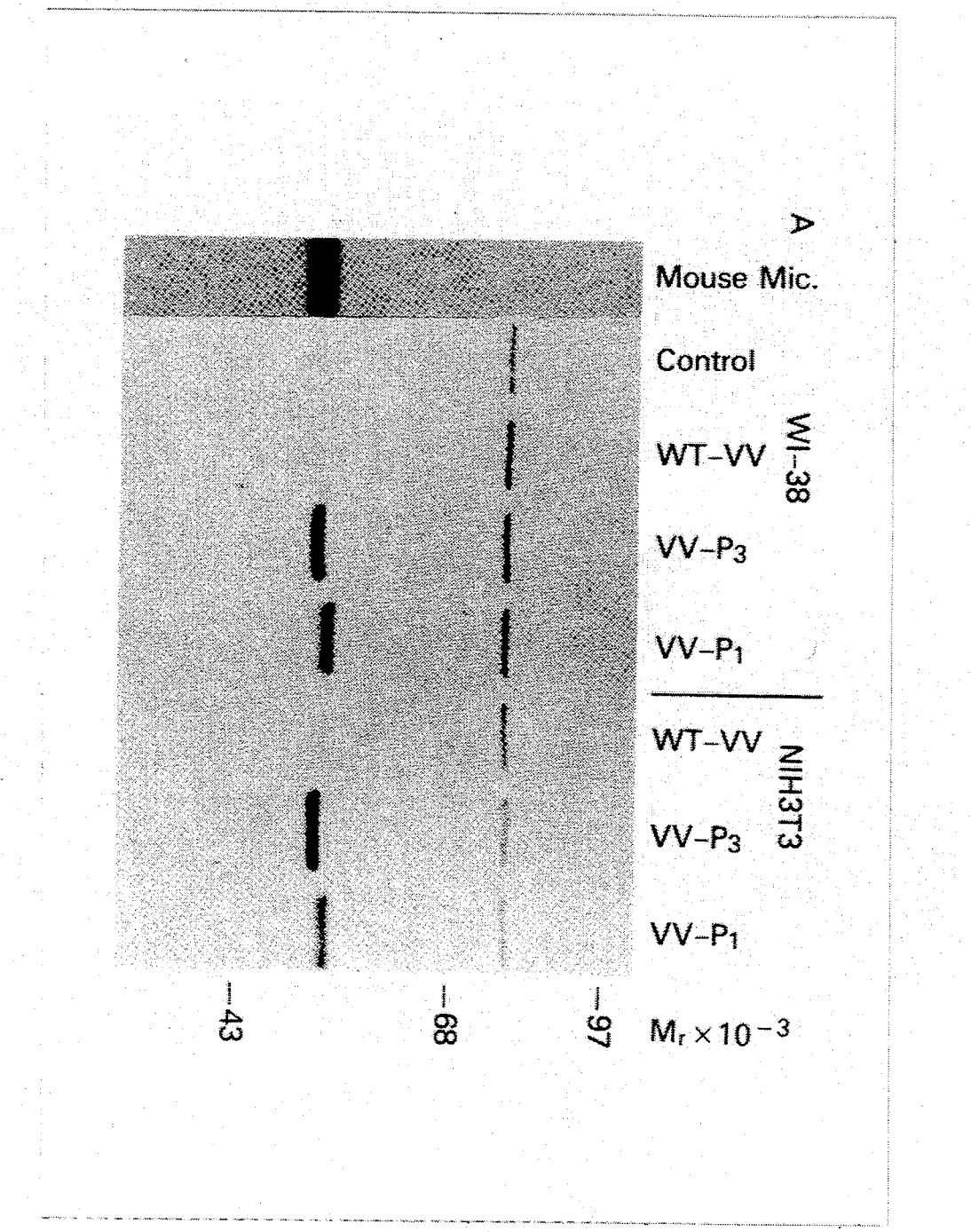
FIG. 2 (parts A and B) demonstrates identification of cytochrome P1-450 and P3-450 polypeptides. Lysates (100 μg) were electrophoresed and detected by immunoblotting. Stained protein molecular weight markers are shown on the right. 2A. Expression in WI-38 and NIH 3T3 cells. 2B. Time course of synthesis in NIH 3T3 cells. The minor $M_r=80,000$ band detected in all cell lanes was not detected when diluted antisera was used.
Figure 2B:
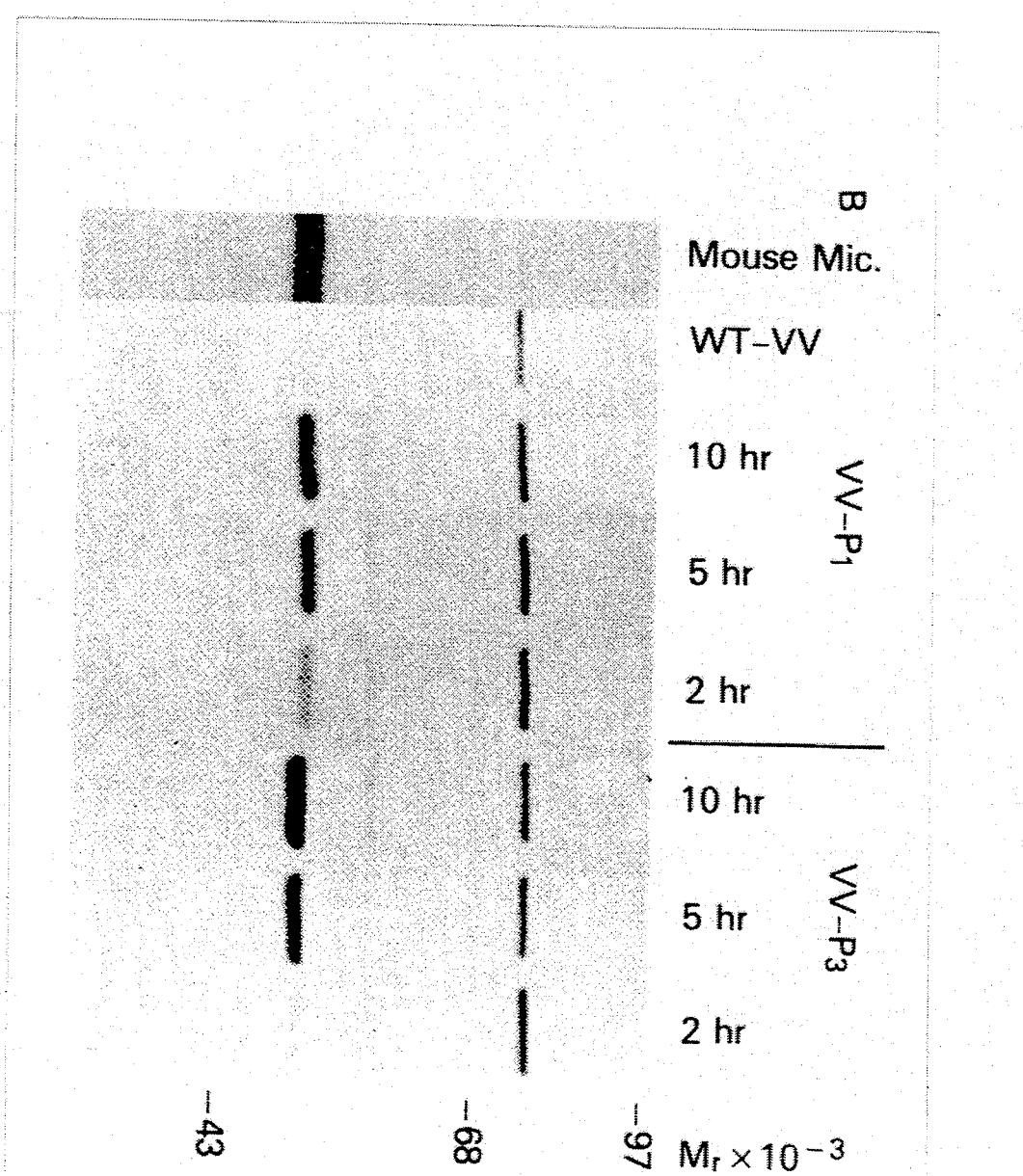

Lysates of human and mouse cells infected with each of the recombinant viruses were electrophoresed on NaDodSO$_4$-polyacrylamide gels and analyzed by immunoblotting (FIG. 2A). Both human WI-38 cells and mouse NIH 3T3 cells infected with the recombinant virus VV-P1 showed a peptide band which cochromatographed with P1-450 of mouse liver microsomes at $M_r \approx 55,000$. These same cells infected with the recombinant virus VV-P3 showed a slightly faster migrating protein band that cochromatographed with P3-450 of mouse liver microsomes at $M_r \approx 54,000$. In lysates of uninfected control cells or cells infected with WT-VV, neither the P1-450 nor the P3-450 bands were detected. The time course of synthesis of P1-450 and P3-450 in virus infected 3T3 cells is shown in the immunoblots in FIG. 2B. Cytochrome P1-450 and P3-450 were detected as early as 2 hours after infection and the amount of the expression product increased during the subsequent 15-hour time interval. Based on the relative intensities of protein bands of P1-450 and P3-450 found in infected human and mouse cells and the P450 contents of the mouse liver microsomes, the specific content is estimated to be in the range of about 15–90 pmoles per mg of infected cells lysates. These results clearly show that the infectious vaccinia virus recombinants directed the synthesis of cytochrome P1-450 and P3-450. The polypeptide products formed were indistinguishable from the active P1-450 and P3-450 of mouse microsomes. The synthesis of the correct size P1-450 and P3-450 polypeptides indicates that no fusion polypeptides were formed nor were any incorrect reading frames expressed. The detection of P450 expression products at an early time after infection is consistent with the use of early vaccinia promoter.

Subcellular Localization of the Newly Synthesized P1-450 and P3-450

Figure 3:
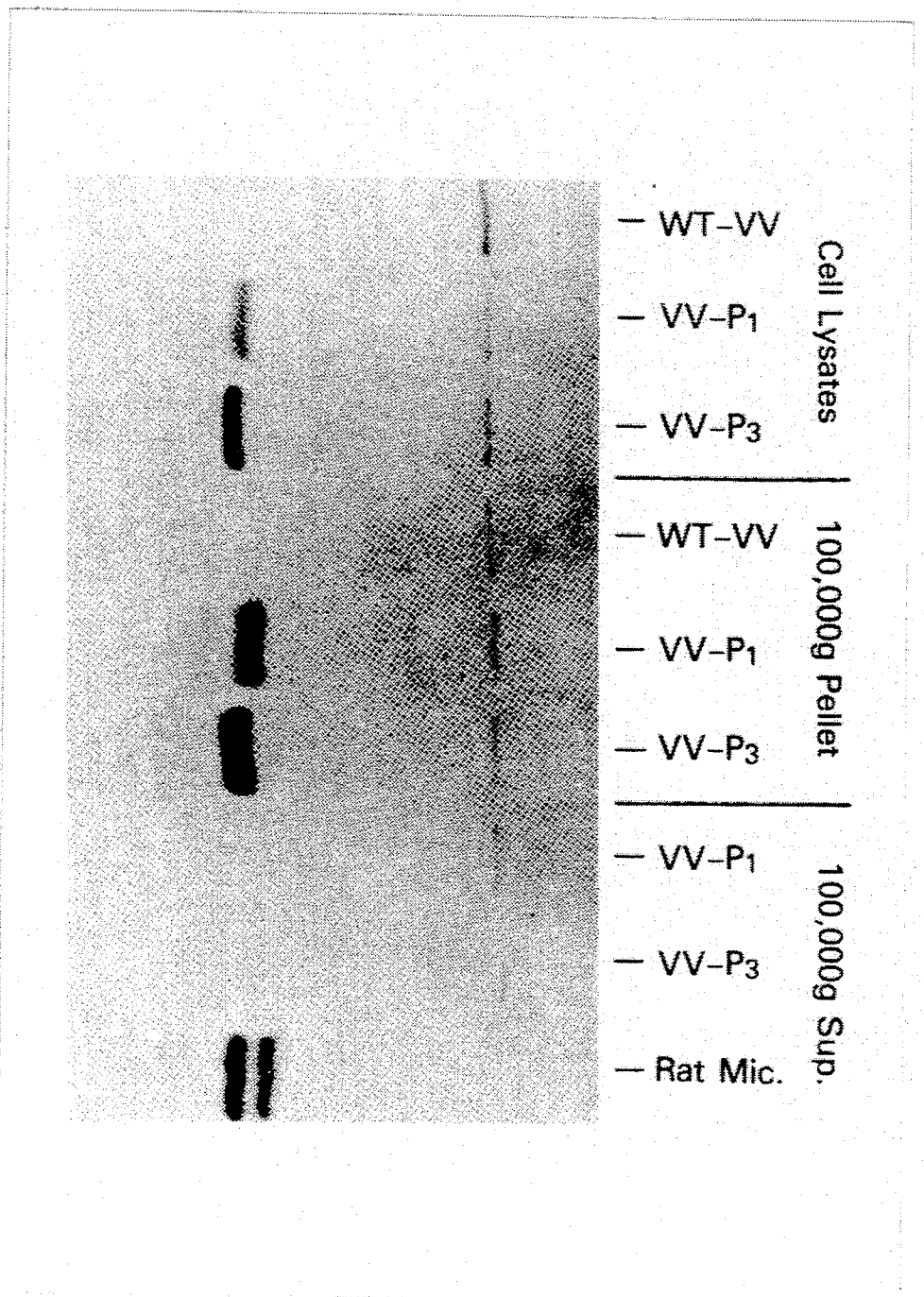
FIG. 3 shows cytochrome P1-450 and P3-450 polypeptides in subcellular fractions. In each lane 100 μg of protein was electrophoresed and immunoblotted.

Native cellular P450 apoproteins normally complex with heme to form hemoproteins which are subsequently transported to microsomal membranes. Therefore, it needed to be determined whether the newly expressed P1-450 and P3-450 likewise are transported to the microsomes in the cell. Hence, the distribution of P1-450 and P3-450 polypeptides in different subcellular fractions of VV-P1 and VV-P3 infected cells was determined by immunoblotting. Results presented in FIG. 3 show that the newly expressed cytochrome P450s were concentrated in the microsomal fraction (100,000 g pellet). Either none or negligible amounts were detected in the 100,000 g supernatant. These results indicated that the cytochrome P450s synthesized by recombinant vaccinia viruses VV-P1 and VV-P3 are translocated to the microsomal membranes. Comparison of the relative band intensities of infected cells lysates and microsomes indicated a ten-fold enrichment of the expressed P450s in the microsomal fraction.

Spectral Characterization of Cytochromes P1-450 and P3-450

Figure 4:
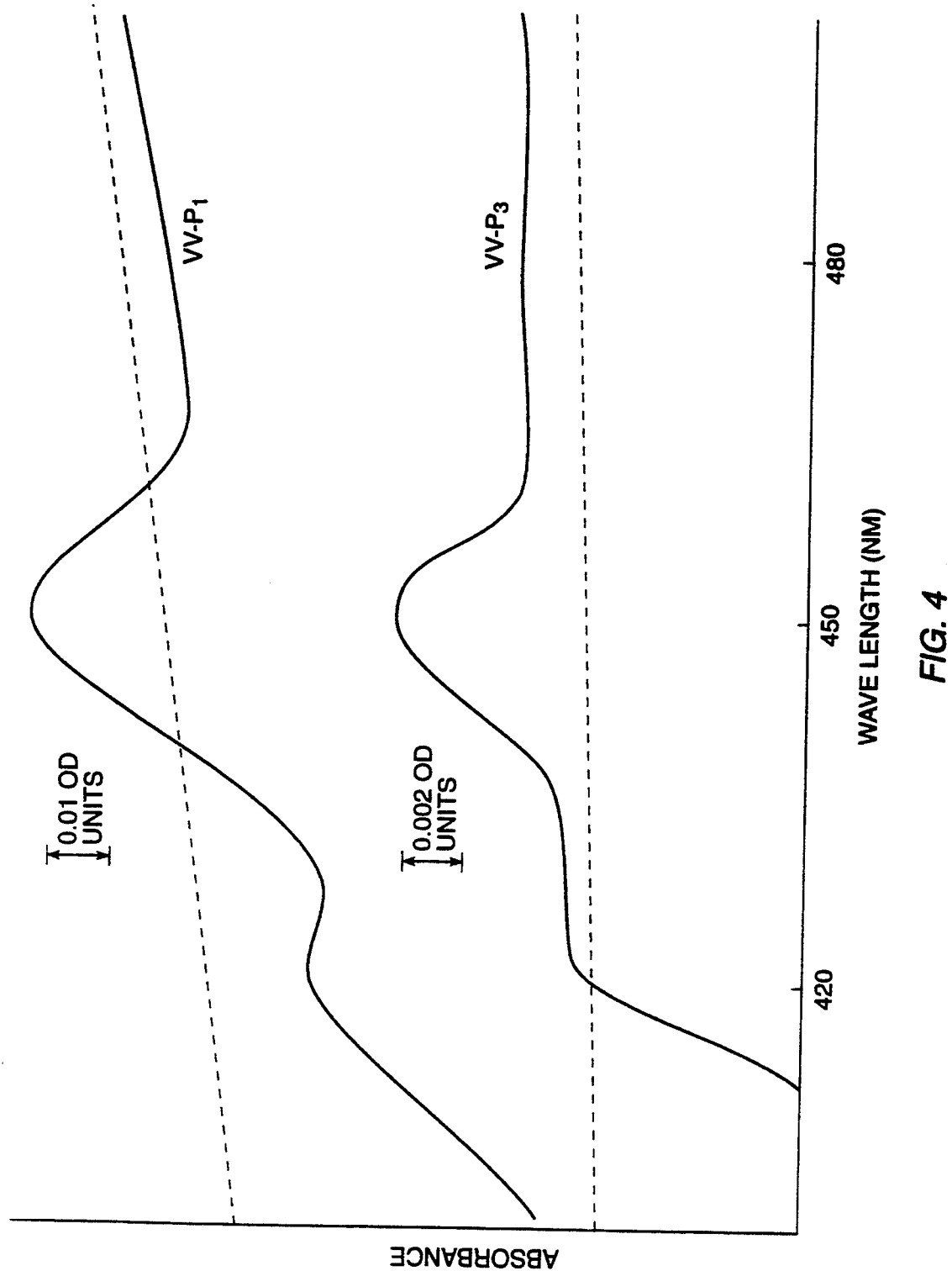
FIG. 4 shows the CO difference spectra of dithionite reduced microsomal fractions. Microsomes were solubilized with emulgen 913 and the supernatant used for spectra. - - - dithionite reduced spectra,—reduced and CO saturated spectra.

A characteristic feature of microsomal cytochrome P450 hemoproteins is that the native catalytically active forms exhibit absorption maxima of reduced CO complex at 450 nm and the denatured catalytically inactive forms exhibit absorption maxima around 420 nm. Examination of the microsomal fraction of NIH 3T3 cells infected with VV-P1 showed an absorption maxima of reduced CO complex at 450 nm indicating that the newly expressed cytochrome P1-450 in microsomes is in native configuration (FIG. 4). Similarly, the microsomal fraction of cells infected with VV-P3 showed a 450 nm peak characteristic of native P450. The specific content of cytochrome P1-450 was 0.028 ng per mg and P3-450 was 0.033 ng per mg of detergent-solubilized microsomal fraction. These results indicate that the cytochrome P1-450 and P3-450 proteins synthesized in virus infected cells incorporate a heme moiety, and are transported and sequestered into the microsomal fraction, in a manner indistinguishable from the native in vivo processed cellular P450s.

Enzyme Activity of P450s in VV-P1 and VV-P3 Infected Cells

Figure 5:
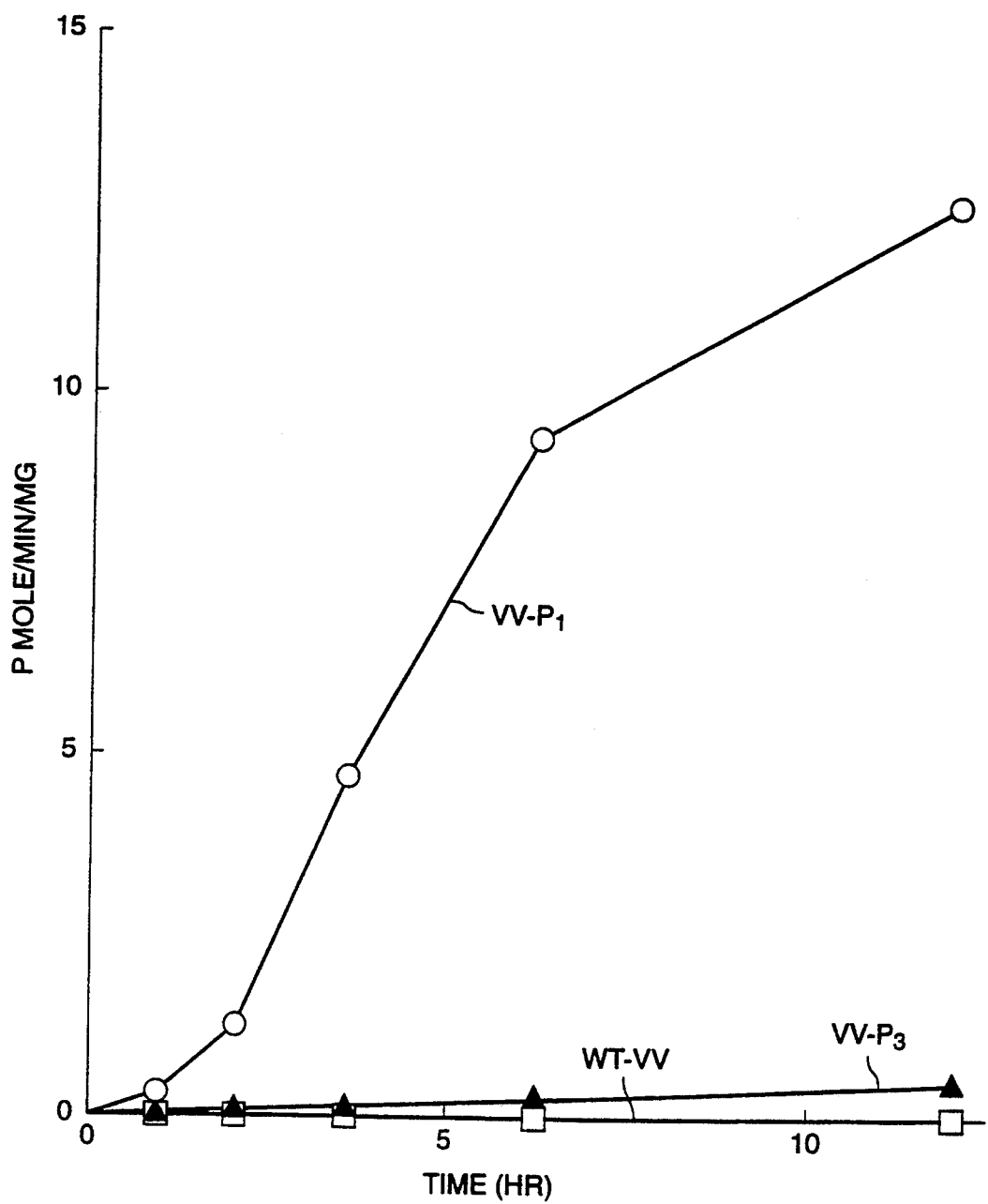
FIG. 5 shows the expression of AHH activity. Infected cells were harvested at the indicated time intervals and lysates assayed for AHH activity. NIH 3T3 cells infected with VV-P1, VV-P3, and WT-VV. No detectable activity was found in uninfected control cells (not shown)

AHH activity in lysates of 3T3 cells infected with VV-P1 shows (FIG. 5) detectable enzyme activity as early as 1 hour after infection and an increase in the enzyme activity for 12 hours thereafter. However, the lysates of cells infected with VV-P3 showed only a small fraction of activity compared to that of VV-P1 even at 12 hours after infection. No detectable activity was found in uninfected control cells or in WT-VV infected cells. The AHH activity was completely inhibited by antisera against P-450c and P-450d (data not shown). The specific AHH activity in different preparations varied in the range of about 10–70 p moles per mg of cell lysates. The AHH activity was at least 30-fold greater with P1-450 than with P3-450.

Figure 6:
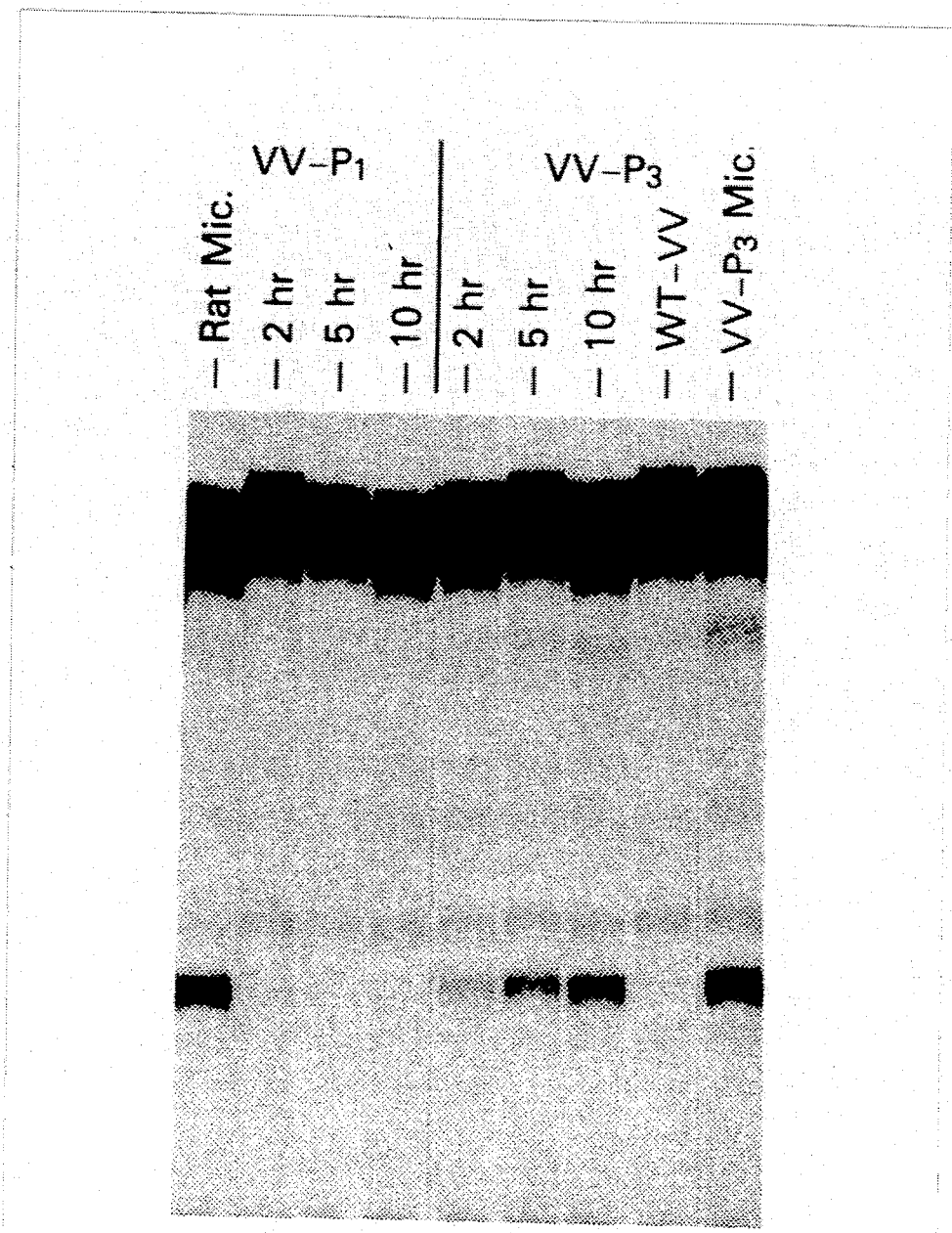
FIG. 6 shows TLC analysis of acetanilide hydroxylase activity. Cell lysates (500 μg) were assayed and the products separated by TLC.

Lysates of 3T3 cells infected with VV-P1 and VV-P3 for different time intervals were assayed for acetanilide hydroxylase activity and the autoradiograms of TLC analysis of the products formed are presented in FIG. 6. Lysates of cells infected with VV-P3, in addition to the intense substrate band (Rf value of 0.74), showed a slow moving band (Rf value of 0.2) identifying the TLC migration position of the hydroxylated products of acetanilide. The formation of hydroxylated metabolites increased with time. In cells infected with VV-P1, however, there was no detectable band at an Rf value of 0.2. No activity was detectable in the control uninfected cells or in cells infected with WT-VV. A minor band at an Rf value of 0.12 was detected in Hepa 1 cells infected with VV-P1 after prolonged exposure (result not shown). The specific acetanilide hydroxylase activity was about 45 pmoles mg of cell lysate. The acetanilide hydroxylase activity was at least 20-fold greater with P3-450 than with P1-450.

The assembly of the holoenzyme and expression of enzyme activity without the necessity of extraneous addition of any coenzyme or cofactor and the like, clearly show that the P1-450 and P3-450 proteins encoded by recombinant virus infected cells are synthesized as a complete catalytically active molecule. In contrast, it should be noted that P450 cytochromes prepared by conventional means do not exhibit enzyme activity unless NADPH cytochrome P450 reductase and other cell fractions are extraneously added (Goldstein, et al., *J. Biol. Chem.*, 257:2702, 1982; Guengerich, et al., *Biochem*, 21:6019–6030, 1982; Negishi, et al., *J. Biol. Chem.*, 254:11015–11023, 1979). Moreover, the cytochrome P1-450 of the present invention has 30–40 fold higher AHH activity than P3-450 and cytochrome P3-450 showed a 20-fold high acetanilide hydroxylase activity than P1-450, a characteristic and distinguishing feature of these two enzymes. Cells infected with recombinant viruses expressed $10^7$–$10^8$ molecules of the newly synthesized cytochromes per cell and this represents 0.1–1.0% of total cellular proteins.

The availability of functionally intact, pure P1-450 and P3-450 enzyme in accordance with the present invention now makes it possible for the first time to test in vitro the metabolism, detoxification, mutagenesis or activation of xenobiotic and endobiotic substances. Availability of such a pure enzymatic system significantly facilitates the testing and development of new drugs, testing carcinogen metabolism, environmental chemical mutagens and the like without resorting to expensive and the time consuming in vivo systems. Furthermore, the recombinant vaccinia virus expression system of the present invention provides an easy, efficient and economical method of producing large quantities of pure catalytically active cytochrome P450 enzymes which was not heretofore possible. To obtain pure P1-450 or P3-450 enzymes, mammalian or other suitable cells are simply infected with recombinant vaccinia virus of the present invention and the infected cells are used directly as a source of P1-450 or P3-450 enzyme which are synthesized as a result of the infection. Alternatively, the microsomal or endoplasmic reticulum fraction of the transfected cells can be separated and used as a source of the pure enzyme.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A non-tumorigenic, immortalized, human bronchial epithelial cell line which expresses an exogenous cytochrome P450 gene contained in said cell line, wherein said cell line is produced by introducing said exogenous cytochrome P450 gene into a BEAS-2B cell line deposited as ATCC CRL 9609.

2. A non-tumorigenic, immortalized human bronchial epithelial cell line, which is designated BEAS-2B-IA2, which is a BEAS-2B cell line transfected with the IA2 cytochrome P450 gene.

3. A diagnostic kit comprising the cell line of claim 1.